(12) United States Patent
Haldis et al.

(10) Patent No.: US 11,801,363 B2
(45) Date of Patent: *Oct. 31, 2023

(54) SLIDE GUIDE CATHETER AND METHODS FOR USE THEREOF

(71) Applicant: Sanford Health, Sioux Falls, SD (US)

(72) Inventors: Thomas Haldis, Sioux Falls, SD (US); Alexander Drofa, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 136 days.

This patent is subject to a terminal disclaimer.

(21) Appl. No.: 17/308,103

(22) Filed: May 5, 2021

(65) Prior Publication Data

US 2021/0252252 A1 Aug. 19, 2021

Related U.S. Application Data

(63) Continuation of application No. 15/836,152, filed on Dec. 8, 2017, now Pat. No. 11,027,093.

(60) Provisional application No. 62/431,624, filed on Dec. 8, 2016.

(51) Int. Cl.
  *A61M 25/00* (2006.01)
  *A61M 25/09* (2006.01)
  *A61M 25/01* (2006.01)
  *A61M 25/06* (2006.01)

(52) U.S. Cl.
  CPC .... *A61M 25/0026* (2013.01); *A61M 25/0043* (2013.01); *A61M 25/0068* (2013.01); *A61M 25/0113* (2013.01); *A61M 25/0662* (2013.01); *A61M 25/09* (2013.01); *A61M 25/008* (2013.01); *A61M 2025/0004* (2013.01); *A61M 2025/0006* (2013.01); *A61M 2025/0175* (2013.01); *A61M 2025/0687* (2013.01)

(58) Field of Classification Search
  CPC ...... A61M 2025/0175; A61M 25/0113; A61M 25/0026; A61M 25/0043; A61M 25/0068; A61M 25/0069; A61M 2025/0687; A61M 25/008; A61M 25/09; A61M 25/0662; A61M 2025/0004; A61M 2025/0006
  See application file for complete search history.

(56) References Cited

U.S. PATENT DOCUMENTS

| | | |
|---|---|---|
| 2,688,329 A | 9/1954 | Wallace |
| 4,586,923 A | 5/1986 | Gould |
| 4,772,266 A * | 9/1988 | Groshong ......... A61M 25/0668 604/164.05 |

(Continued)

OTHER PUBLICATIONS

International Search Report and Written Opinion for PCT Application No. PCT/US2017/065337, dated Mar. 22, 2018*.

*Primary Examiner* — Theodore J Stigell (74) *Attorney, Agent, or Firm* — MCDONNELL BOEHNEN HULBERT & BERGHOFF LLP (57) ABSTRACT

The present disclosure provides a catheter system and methods for use that includes (a) a first catheter having a first end and a second end, where the first catheter has a first diameter, (b) a second catheter having a first end and a second end, where the second catheter has a second diameter that is less than the first diameter of the first catheter, and where the second catheter is positioned at least partially within a lumen of the first catheter and is moveable relative to the first catheter, and (c) a wire having a first end and a second end, where the first end of the wire is coupled to the second catheter.

37 Claims, 5 Drawing Sheets

(56) References Cited

U.S. PATENT DOCUMENTS

| | | | |
|---|---|---|---|
| 4,883,058 A | | 11/1989 | Ruiz |
| 4,976,688 A | | 12/1990 | Rosenblum |
| 5,120,323 A | * | 6/1992 | Shockey ............... A61M 25/01 |
| | | | 604/528 |
| 5,415,636 A | * | 5/1995 | Forman ............... A61M 25/104 |
| | | | 604/101.03 |
| 5,533,985 A | * | 7/1996 | Wang ...................... B29C 48/21 |
| | | | 604/525 |
| 5,658,264 A | | 8/1997 | Samson |
| 5,658,309 A | | 8/1997 | Berthiaume |
| 5,681,344 A | | 10/1997 | Kelly |
| 6,585,694 B1 | * | 7/2003 | Smith ............... A61M 25/0084 |
| | | | 604/164.12 |
| 6,592,567 B1 | * | 7/2003 | Levin ................... A61M 25/10 |
| | | | 604/509 |
| 8,206,343 B2 | | 6/2012 | Racz |
| 10,716,915 B2 | | 7/2020 | Ogle |
| 11,027,093 B2 | * | 6/2021 | Haldis ............... A61M 25/0113 |
| 2005/0004553 A1 | | 1/2005 | Douk |
| 2005/0272975 A1 | * | 12/2005 | McWeeney ....... A61M 25/0068 |
| | | | 600/172 |
| 2007/0260219 A1 | | 11/2007 | Root |
| 2010/0030186 A1 | | 2/2010 | Stivland |
| 2010/0168785 A1 | | 7/2010 | Parker |
| 2018/0133007 A1 | | 5/2018 | Prabhu |
| 2020/0276411 A1 | | 9/2020 | Ogle |

* cited by examiner

SLIDE GUIDE CATHETER AND METHODS FOR USE THEREOF

CROSS-REFERENCE TO RELATED APPLICATIONS

This application is a continuation of U.S. Non-Provisional application Ser. No. 15/836,152 entitled "Slide Guide Catheter and Methods for Use Thereof", filed on Dec. 8, 2017 that claims the benefit of priority to U.S. Provisional Application No. 62/431,624 entitled "Slide Guide Catheter," filed on Dec. 8, 2016, the contents of each of which are hereby incorporated by reference in their entirety.

BACKGROUND OF THE INVENTION

Cerebral blood flow is critical in human anatomy. If blood flow is blocked to the brain, the tissue that does not receive blood flow will become ischemic and begin to die. The result is either a deficit in cognition, function, or even death. The results are also irreversible if such an ischemia lasts too long. The period of time can vary from patient to patient, but typically if blood flow to the brain is not restored after approximately 4.5 hours, an ischemic stroke may occur. These ischemic strokes can happen in any of the cerebral arteries, but are most common in the middle cerebral artery. Traditionally, such middle cerebral artery acute ischemic strokes have been fatal.

Around 1995, the use of tissue plasminogen activator (tPA), a lytic agent, was introduced as the first treatment for ischemic stroke. The tPA brakes down unorganized acute clot. This procedure reduced mortality from near 100% to 80% and has been the main stay in acute ischemic stroke treatment until just recently. In 2015, a new approach was approved in the United States known as mechanical thrombectomy. In this approach, a stent retriever is deployed within a lesion, the stent struts spread into the clot, then the clot is drawn back into the catheter under suction and removed from the body. This mechanical thrombectomy approach has reduced the mortality rate to around 20% for patients who are treated within the critical time window.

While outcomes are significantly improved, the mechanical thrombectomy procedure is still labor intensive. The mechanical thrombectomy device is either introduced through a femoral or carotid access. If the device is introduced from a femoral access, the operator needs to navigate the aortic anatomy with a special focus on the aortic arch. Aortic arches can be difficult to navigate, especially with type three aortic arches. Once the lesion is reached and crossed, the lesion can be treated. However, reaching the lesion can be challenging due to the tortuous nature of various arteries, such as the cerebral and coronary arteries as examples. The guide catheter which is used to select the target artery is often too stiff and has too large of a diameter to pass the bends in the middle cerebral artery and/or coronary arteries, pulmonary arteries and venous system.

SUMMARY OF THE INVENTION

An improved catheter system is described herein to improve navigation within the lumens of arteries and veins, including tortuous bends, for example.

In particular, in a first aspect, the present disclosure provides a catheter system comprising: (a) a first catheter having a first end and a second end, where the first catheter has a first diameter, (b) a second catheter having a first end and a second end, where the second catheter has a second diameter that is less than the first diameter of the first catheter, and where the second catheter is positioned at least partially within a lumen of the first catheter and is moveable relative to the first catheter, and (c) a wire having a first end and a second end, where the first end of the wire is coupled to the second catheter.

In a second aspect, the present disclosure provides a method comprising: (a) introducing a guidewire into an arterial or venous configuration via arterial or venous access, (b) loading the catheter system of the first aspect onto the guidewire, (c) moving the catheter system along the guidewire and introducing the first catheter into a first arterial configuration, and (d) advancing, using the wire of the catheter system, the second catheter with respect to the first catheter to move the second catheter into a second arterial configuration.

The features, functions, and advantages that have been discussed can be achieved independently in various examples or may be combined in yet other examples, further details of which can be seen with reference to the following description and drawings.

BRIEF DESCRIPTION OF THE DRAWINGS

Examples are described below in conjunction with the appended figures, wherein like reference numerals refer to like elements in the various figures, and wherein.

Corresponding parts are marked with the same reference symbols in all figures.

The drawings are provided for the purpose of illustrating examples, but it is understood that the examples are not limited to the arrangements and instrumentalities shown in the drawings.

DETAILED DESCRIPTION

As used herein, with respect to measurements, "about" means+/−5%.

As used herein, a "catheter" is an apparatus that is connected to a deployment mechanism and houses a medical device that can be delivered over a guidewire. The catheter may include a guidewire lumen for over-the-wire guidance and may be used for delivering a device to a target lumen. A catheter can have braided metal strands within the catheter wall for increased structural integrity. The structural elements of the catheter tip can be bonded or laser welded to the braided strands of the catheter to improve the performance characteristics of the catheter tip.

As used herein, a "guidewire" is an elongated cable comprised of one or more biocompatible materials including metals and polymers. Guidewires may be used for selecting target lumens and guiding catheters to target deployment locations. Guidewires are typically defined as wires used independently of other devices that do not come as part of an assembly.

As used herein, a "stent retriever" is a device, like a stent, that is advanced through emboli and allowed to expand and embed in the emboli that may then be retracted to restore blood flow and aid thrombectomy in acute embolic stroke.

As used herein, "lumen" refers to a passage within an arterial structure, such as the pulmonary arteries or a passage within the tubular housings or catheters through which the guidewire may be disposed.

As used herein, "deployment" refers to when a catheter has been positioned in the target lumen and is actively being used.

As used herein, "first end" refers to a distal end of the device or component thereof, and "second end" refers to a proximal end of the device or component thereof.

As used herein, "distal" with respect to a portion of the apparatus means the end of the device (when in use) nearer the treatment zone (e.g., the pulmonary artery) of the subject and the term "proximal" means the portion of the device (when in use) further away from the targeted lumen of the subject and nearer the access site and the operator.

Exemplary catheter systems and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Thus, in a first aspect, the present disclosure provides a catheter system that includes a first catheter having a first end and a second end, wherein the first catheter has a first diameter, (b) a second catheter having a first end and a second end, wherein the second catheter has a second diameter that is less than the first diameter of the first catheter, and wherein the second catheter is positioned at least partially within a lumen of the first catheter and is moveable relative to the first catheter, and (c) a wire having a first end and a second end, wherein the first end of the wire is coupled to the second catheter.

In a second aspect, the present invention disclosure provides a method comprising: (a) introducing a guidewire into an arterial configuration via arterial access, (b) loading the catheter system of the first aspect onto the guidewire, (c) moving the catheter system along the guidewire and introducing the first catheter into a first arterial configuration, and (d) advancing, using the wire of the catheter system, the second catheter with respect to the first catheter to move the second catheter into a second arterial configuration.

In particular, as shown in FIGS. 1-4, an example catheter system 100 includes a first catheter 105 having a first end 110 and a second end 111. The first catheter 105 has a length that ranges from about 60 cm to about 110 cm, for example. The first catheter 105 also has a first diameter that ranges from about 1.33 mm to about 9.0 mm, for example. Larger diameters may be used to account for treatments providing venous and pulmonary clot retrieval. The first diameter corresponds to an inner diameter. A portion of the first catheter 105 at the first end 110 may optionally include one or more curved sections, such as a first bend and a second bend, as one example. The first bend and the second bend may accommodate curves of the target arterial configuration, such as the pulmonary, coronary artery or cerebral artery, as examples.

The catheter system 100 further includes a second catheter 115 having a first end 120 and a second end 121. The second catheter 115 has a length ranging from about 10 cm to about 55 cm, for example. The second catheter 115 also has a second diameter that is less than the first diameter of the first catheter 105. In particular, the second diameter may range from about 1 mm to about 8.7 mm. Larger diameters may be used to account for treatments providing venous and pulmonary clot retrieval. The second diameter corresponds to an outer diameter. The second catheter 115 may be positioned at least partially within a lumen 125 of the first catheter 105 and is moveable relative to the first catheter 105.

The catheter system 100 further includes a wire 130 having a first end 135 and a second end 136. The first end 135 of the wire 130 is coupled to the second catheter 115. The wire 130 may be coupled to any portion of the second catheter 115, for example, the first end 120 of the second catheter 115. In operation, the wire 130 is configured to advance the second catheter 115 distally out of the first catheter 105 and to retract the second catheter 115 proximally into the lumen 125 of the first catheter 105. The catheter system 100 may have an overall length in a range of about 70 cm to about 160 cm, for example, when the second catheter 115 is fully extended from the first catheter 105 via the wire 130. The wire 130 includes at least one braided wire, such as a braided stainless steel wire, for example. In another example, the wire 130 may comprise a nitinol wire. In another example, the wire 130 may include a solid or braided wire of any metal or metal alloy. In any of the above examples, the wire 130 may be positioned within a steel tube to provide structural support for the wire 130 when the wire is under compressive forces. In another example, the wire 130 may be positioned within a nitinol tube, thus preventing galvanic corrosion and also introducing a shape memory effect.

In one example, the wall of the first catheter 105 includes a conduit 140 arranged therein in which the wire 130 at least partially resides. In such an example, a first end 141 of the conduit 140 is configured to abut the second end 121 of the second catheter 115 when the second catheter 115 is fully retracted to prevent the first end 120 of the second catheter 115 from retracting past the first end 110 of the first catheter 105 and further into the lumen 125 of the first catheter 105. In an alternative example, an external housing 145 having a conduit 150 is coupled to an exterior of the first catheter 105 such that the wire 130 is disposed within the conduit 150 and extends through an opening 155 in a wall of the first catheter 105 to the second catheter 115.

In one embodiment, a stiffness of a portion of the first catheter 105 at the first end 110 is greater than a stiffness of a portion of the second catheter 115 at the first end 120. In such an example, the first catheter 105 includes a first material, and the second catheter 115 includes a second material that is different than the first material. For example, the first material and the second material may include an elastomer, a metal, a hydrophilic polymer or a combination thereof. In one specific example, the first catheter 105 includes an elastomer outer layer, a metal middle layer (e.g., a braided metal layer), and an inner hydrophilic polymer layer (e.g., PTFE). In a further example, the first catheter 105 has a distal first section 160 at the first end 110 and a proximal second section 165 at the second end, and a pick count of the braided metal layer of the distal first section 160 is lower than a pick count of the braided metal layer of the proximal second section 165. The higher pick count of the distal first section 160 increases flexibility relative to the proximal second section 165, while the lower pick count of the proximal second section 165 increases stiffness, kink-resistance and torque response relative to the distal first section. In another embodiment, the metal layer may include a plurality of braided metal strands arranged longitudinally or helically along at least a portion of the length of the first catheter 105. In still another embodiment, the elastomer outer layer has a durometer in the distal first section 160 that is lower than a durometer of the proximal second section 165. The lower durometer of the distal first section 160 may increase flexibility and tractability relative to the proximal second section 165, while the higher durometer of the proximal second section 165 may increase stiffness, kink-resistance and torque response relative to the distal first section 160. The inner hydrophilic polymer layer results in a lubricious coating and reduces friction between the first catheter 105 and second catheter 115 thereby facilitating passage of the second catheter 115 through lumen 125. In such an example, the second catheter 115 may include an elastomer outer layer and an inner hydrophilic polymer layer (e.g., PTFE). As such, the second catheter 115 may not include a braided metal layer.

In another example, a wall thickness of a portion of the second catheter 115 at the first end 120 may be less than a wall thickness of a portion of the first catheter 105 at the first end 110. In such an example, the first catheter 105 and the second catheter 115 may comprise the same material(s), and the varying thicknesses provide the difference in stiffness. In another example, as described above, the thickness of the first catheter 105 and the second catheter 115 may be the same, while the difference in material(s) provides the difference in stiffness between the two components. In another example, the first and second catheters 105, 115 have differential stiffness throughout; the second end 111, 121 (i.e., proximal) may be the stiffest and gradually softens towards the first end 110, 120 (i.e., distal tip). In such an example, the portion of the second catheter 115 at the first end 120 may be less stiff than the portion of the first catheter 105 at the first end 110. In one example, at least one of the first catheter 105 and the second catheter 115 include a hydrophilic coating.

The respective stiffness of the first and second materials may be controlled by the selected materials or respective thicknesses, as described above. As the second catheter 115 is smaller in diameter and may be less stiff than the first catheter 105, and this arrangement will minimize the risk of creating vascular trauma such as dissections or perforations. At times during a surgical procedure, more support may be needed in order to advance the catheter system 100, and at these times the second catheter 115 may be retracted within the first catheter 105 so that the first catheter 105 can provide the mechanical support required to advance the catheter system 100. At other times during the surgical procedure, such as when the catheter system 100 must pass through tortuous arteries, the second catheter 115 may be extended with respect to the first catheter 105 so that the second catheter 115 passes through such arteries. In one particular example, when the catheter system 100 must pass the bends in the cerebral artery, the second catheter 115 may be extended with respect to the first catheter 105 so that the second catheter 115 passes through cerebral artery tortuosity. In another example, the first catheter 105 may be used to engage the coronary artery. In such an example, the second catheter 115 may be advanced into the coronary artery around bends and calcification to facilitate delivery of coronary balloons and stents and for thrombectomy and delivery of intracoronary medications. Other example uses are possible as well.

Figure 1:
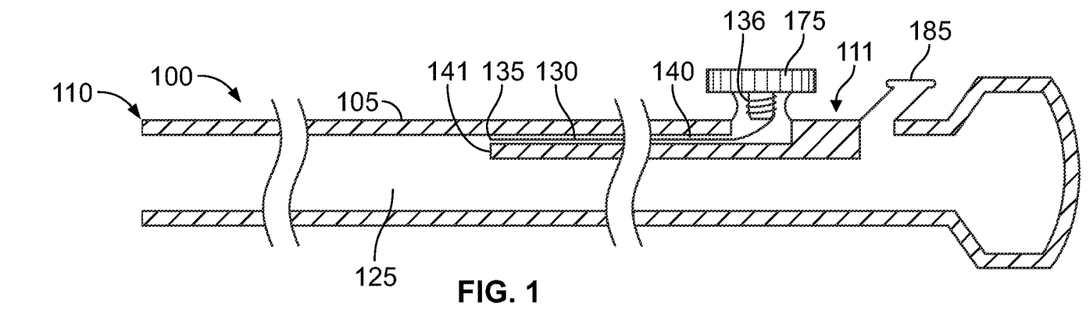
FIG. 1 is a side cross-sectional view of a first catheter of a deployment device, according to an example embodiment.
Figure 2:
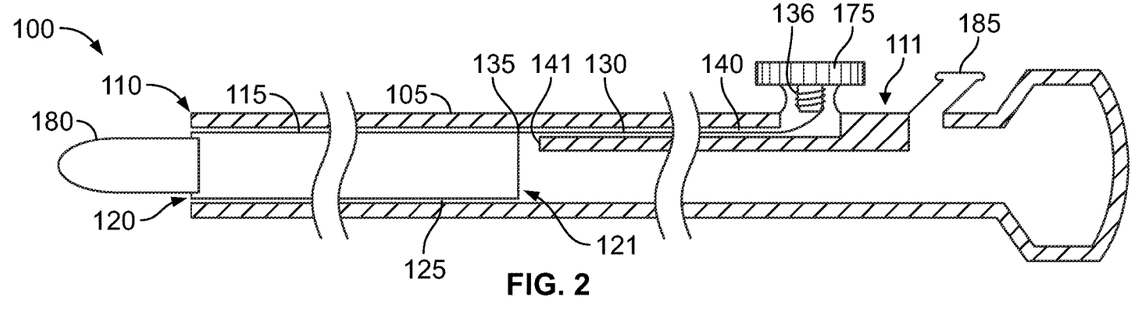
FIG. 2 is side cross-sectional view of the deployment device according to FIG. 1 with a second catheter positioned in a retracted position within the first catheter.
Figure 3:
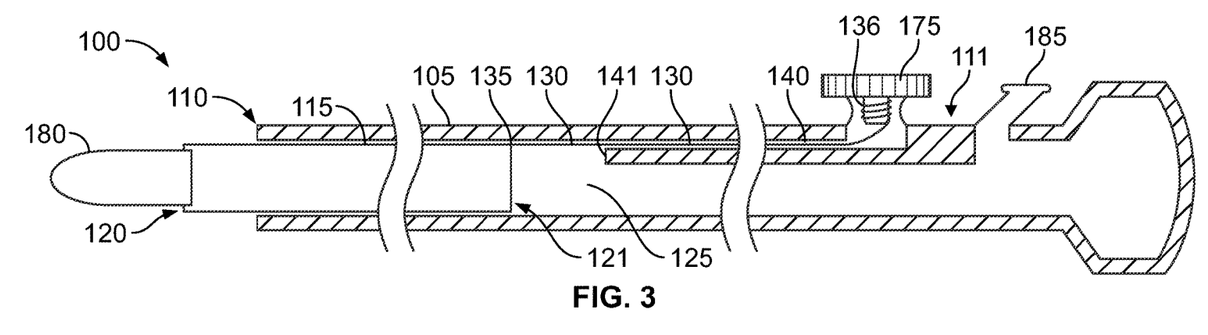
FIG. 3 is a side cross-sectional view of the deployment device according to FIG. 1 with a second catheter advancing out of the first end of the first catheter.
Figure 4:
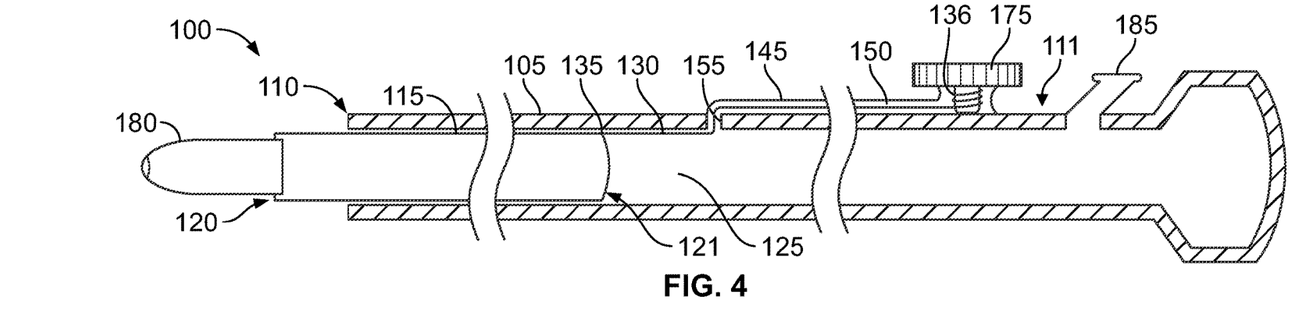
FIG. 4 is a side cross-sectional view of a deployment device, according to an example embodiment.
Figure 5:
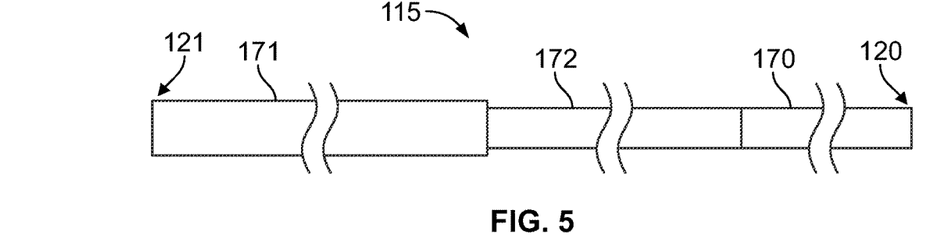
FIG. 5 is a side view of the second catheter according to an example embodiment.

In an optional embodiment, shown in FIG. 5, the second catheter 115 has a first portion 170 arranged at the first end 120, a second portion 171 arranged at the second end 121 and a third portion 172 arranged therebetween. In various examples, the second portion 171 of the second catheter 115 has a length ranging from about 80 cm to about 82 cm, the third portion 172 of the second catheter 115 has a length ranging from about 28 cm to about 30 cm, and the first portion 170 of the second catheter 115 has a length ranging from about 17 cm to about 19 cm. In a further embodiment, the first portion 170 of the second catheter 115 has a durometer less than a durometer of the third portion 172 of the second catheter 115 and the durometer of the third portion 172 of the second catheter 115 is less than the durometer of the second portion 171 of the second catheter 115. In another example, an outer diameter of the first portion 170 of the second catheter 115 is the same as an outer diameter of the third portion 172 of the second catheter 115. In a further example, an outer diameter of the second portion 171 of the second catheter 115 is greater than the outer diameter of the first portion 170 and the outer diameter of the third portion 172 of the second catheter 115.

Figure 7:
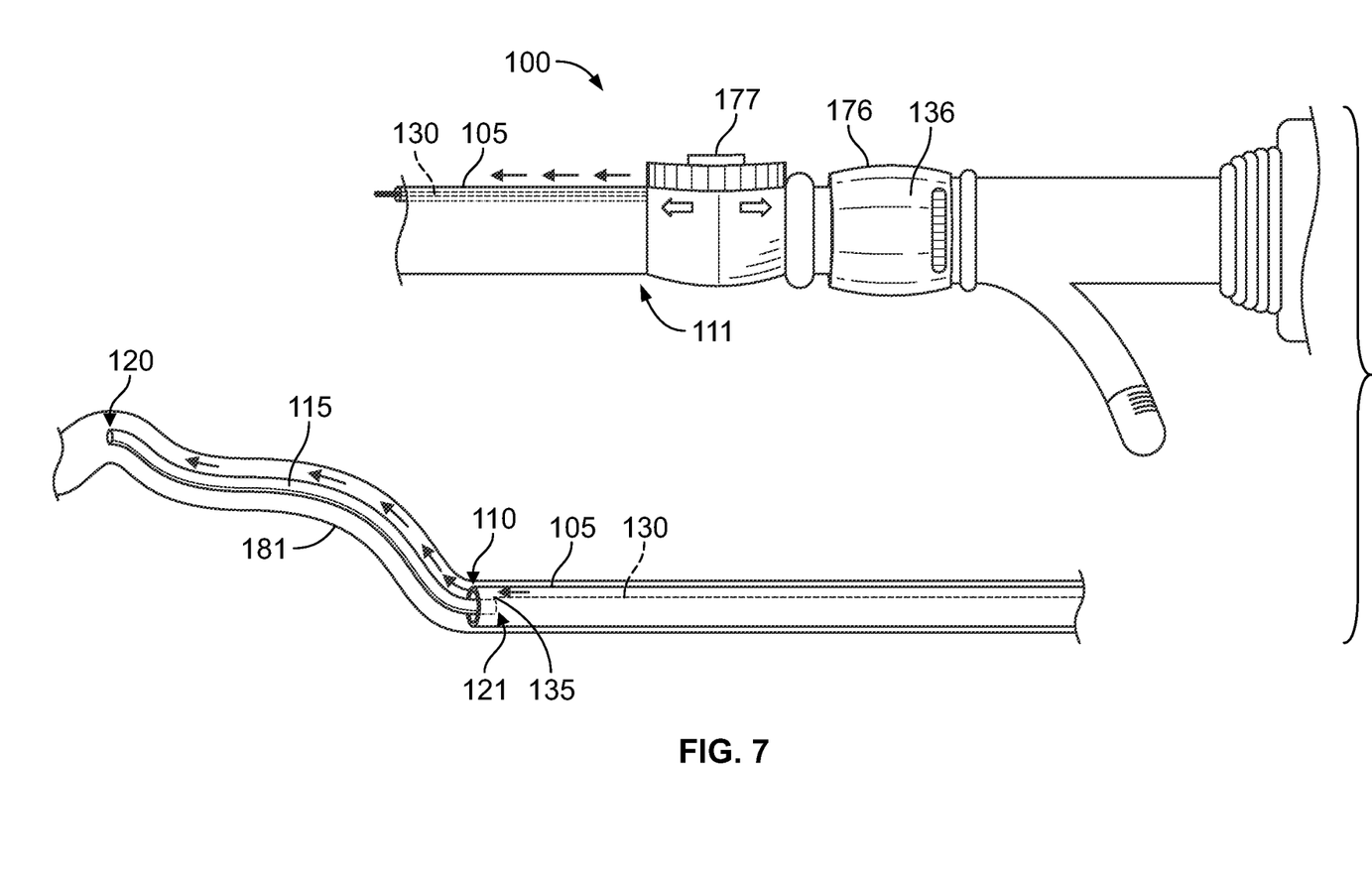
FIG. 7 is a perspective view of the catheter system according to FIGS. 1-3 deployed in an arterial configuration with the second catheter advanced out of the first catheter.
Figure 8:
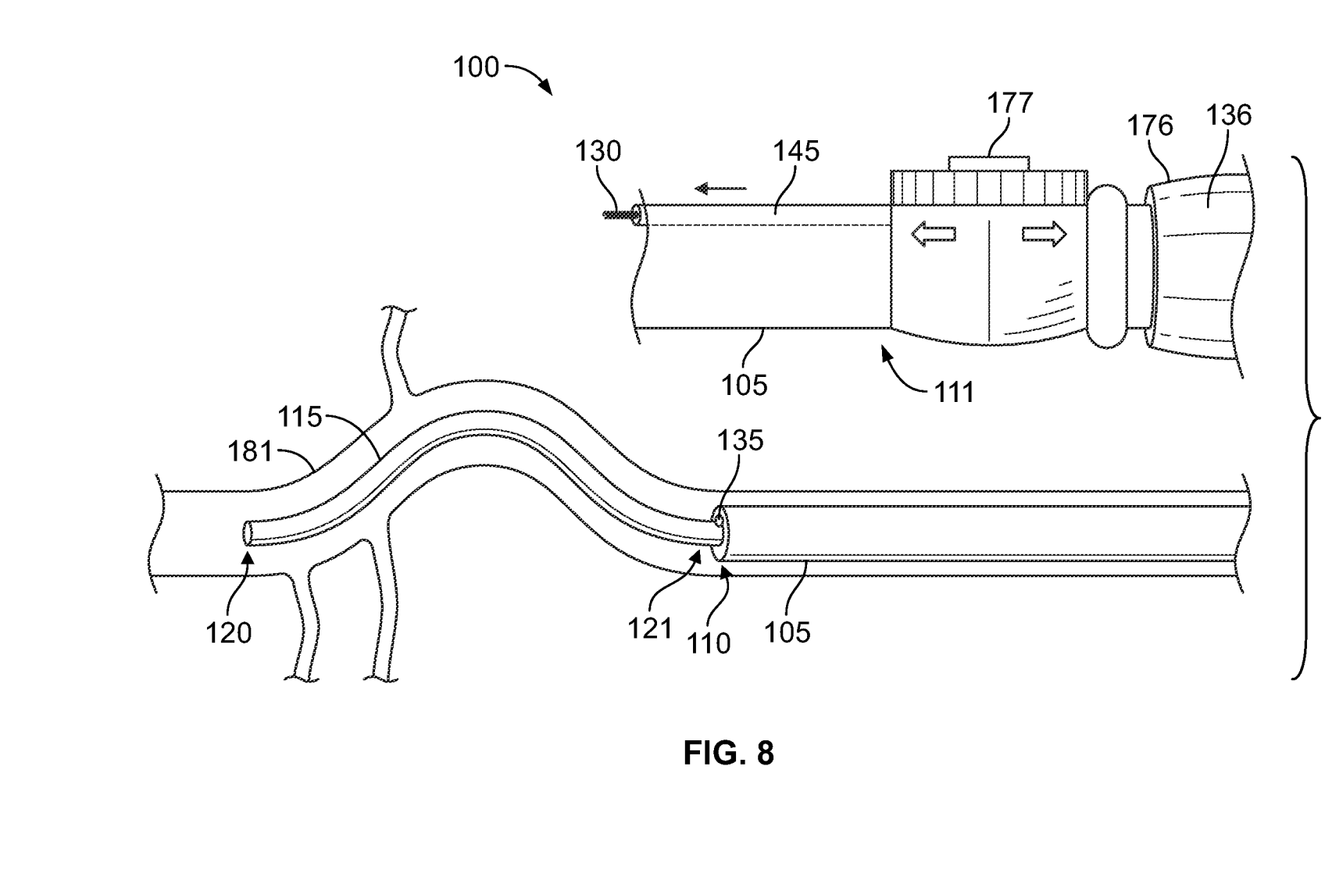
FIG. 8 is a side view of the catheter system according to FIG. 4 deployed in an arterial configuration with the second catheter advanced out of the first catheter.

The catheter system 100 may include a mechanism to cause the second catheter 115 to move with respect to the first catheter 105 (i.e., advance out of or retract into the lumen 125 of the first catheter 105). In one example, shown in FIGS. 1-3, the second end 136 of the wire 130 is coupled to a threaded knob 175 configured to rotate such that, when the wire 130 is unwound from the threaded knob 175, the second catheter 115 is advanced out of the first catheter 105 and, when the wire 130 is wound around the threaded knob 175, the second catheter 115 is retracted into the first catheter 105. In another example, the second end 136 of the wire 130 is coupled to a linear slide configured to move the wire 130 to cause the second catheter 115 to move with respect to the first catheter 105. In another example, shown in FIGS. 7-8, the second end 136 of the wire 130 is coupled to a spooled wire system such that unwinding the spooled wire system 176, via a thumbwheel 177 for example, advances the wire 130 to cause the second catheter 115 to move with respect to the first catheter 105. FIGS. 7 and 8 show the catheter system 100 deployed in an arterial configuration with the second catheter 115 advanced out of the first catheter 105. In particular, FIG. 7 shows an embodiment in which the wall of the first catheter 105 includes a conduit 140 arranged therein in which the wire 130 at least partially resides. FIG. 8 shows one alternative embodiment in which an external housing 145 having a conduit 150 is coupled to an exterior of the first catheter 105 such that the wire 130 is disposed within the conduit 150 and extends through an opening 155 in a wall of the first catheter 105 to the second catheter 115.

Figure 9:
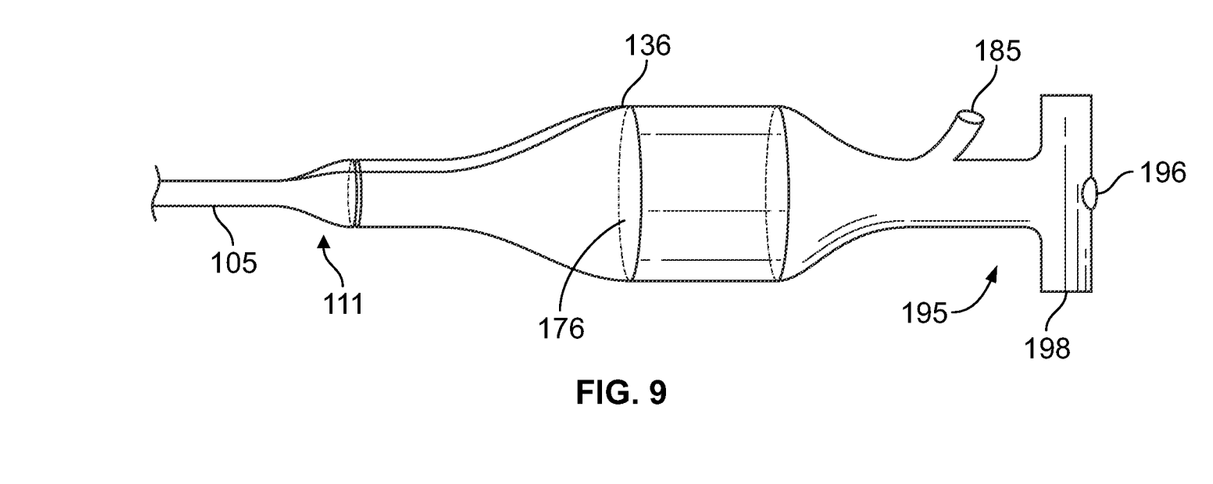
FIG. 9 is a side view of a locking system for the catheter system according to one embodiment.
Figure 10:
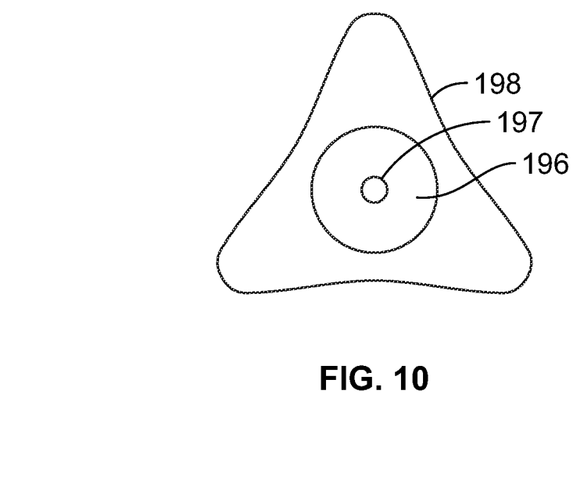
FIG. 10 is an end view of the locking system of FIG. 9.

The catheter system 100 may further include a locking system configured to lock the second catheter 115 in place. In one example, the locking system may include a friction or ratcheting break to prevent the wire 130 and or wire advancement mechanism from moving spontaneously. In another example, the locking system may include a tightening nut in the case of the spooled wire system. When the tightening nut is tightened, the spool is unable to rotate, thereby preventing the wire 130 from being wound around the spool to thereby prevent the second catheter 115 from moving with respect to the first catheter 105. In another example, shown in FIGS. 9-10, the locking system 195 may include a tuohy-borst adapter 196 that can be tightened over an externalized part of the wire 130. Such a tuohy-borst adapter 196 may also include a torque lock, locking nut, or a hemostatic valve. In use, the wire 130 may pass through a center 197 of the tuohy-borst adapter 196, and a rotatable component, such as turn-key 198, may be rotated to thereby tighten the tuohy-borst adapter 196 around the wire to prevent the second catheter 115 from moving with respect to the first catheter 105. In yet another example, the locking system may include a linear press-and-advance system. In such a configuration, the wire 130 is coupled to a slide, and the slide is coupled to a housing. The housing may remain stationary with respect to the first catheter 105, such that the second catheter 115 only moves with respect to the first catheter 105 when the slide moves with respect to the housing. In another example, the mechanism may be a wire 130 that is externalized through the conduit 140 in the first catheter 105 and that is configured to be manually retracted or advanced.

The first catheter 105 may be in mechanical communication with the second catheter 115 in a number of arrangements. In one example, the first catheter 105 is in mechanical communication with the second catheter 115 via a gear system comprising a first gear coupled to the first catheter 105 and a second gear coupled to the second catheter 115. In such an example, an axis of rotation of the first gear may be positioned perpendicular to an axis of rotation of the second gear such that a rotation of the first gear translates to a linear movement of the second catheter 115 with respect to the first catheter 105. In another example, the first catheter 105 is in mechanical communication with the second catheter 115 via a rack and pinion system. Other example arrangements are possible as well. These examples also include a wire 130 that is configured to directly control the second catheter 115 (i.e., no additional mechanisms mediating the movement of the catheter are necessary).

The catheter system 100 optionally includes a dilator 180 coupled to the first end 120 of the second catheter 115. In one embodiment, the dilator 180 has a length at least about 5 cm longer than an overall length of the catheter system 100 when the second catheter 115 is fully extended out of the lumen 125 of the first catheter 105. The dilator 180 permits effective introduction of the catheter system 100 into the body via a transcutaneous approach. The dilator 180 may be coupled to the second catheter 115 via a touhey mechanism or snap fit, for example. In one embodiment, the dilator 180 may be in the form of a tapered catheter that is longer than the catheter system 100 to accommodate a 0.035, 0.018 or 0.014 inch wire, for example, that fits through the first catheter 105 and second catheter 115 from the first end 120 of the second catheter 115 to the second end 111 of the first catheter 105. The dilator 180 will typically extend beyond the first end 110, 120 of both the first catheter 105 and the second catheter 115 and may be removed via the second end 111 of the first catheter 105 after the catheter system 100 is introduced into the vessel or arterial configuration. The purpose of the dilator 180 is to facilitate percutaneous access and facilitate access into one of the arterial configurations.

Catheters can often be curved on the distal end in order to facilitate selection of branch vessels. The catheter system 100 described herein may be configured to be able to accept a curved "introducer" within the second catheter 115. Also, the catheter system 100 may come with a pre-curved second catheter, a pre-curved first catheter, or both. The radius of curvature may vary in order to navigate the variable patient anatomy. In particular, the first end 110 of the first catheter 105 may have a radius of curvature ranging from about 0 mm to about 170 mm, and the first end 120 of the second catheter 115 has a radius of curvature ranging from about 0 mm to about 170 mm.

Further, the first catheter may include one or more side ports 185 to permit access to the lumen 125 of the first catheter. For example, the first end 120 of the second catheter 115 may be coupled to a drug infusion lumen to provide continuous perfusion of a treatment solution to the treatment area. In another example, the first end 120 of the second catheter 115 may be coupled to a side port through which a treatment solution may pass. In addition, the catheter system may include another port for injection of IV contrast during the surgical procedure. In various non-limiting embodiments, the therapeutic may comprise sirolimus, heparin, and cell-based therapies; and antineoplastic, anti-inflammatory, antiplatelet, anticoagulant, antifibrin, antithrombin, antimitotic, antibiotic, vasodialate, antiallergic thrombolytic and antioxidant sub stances.

Figure 6:
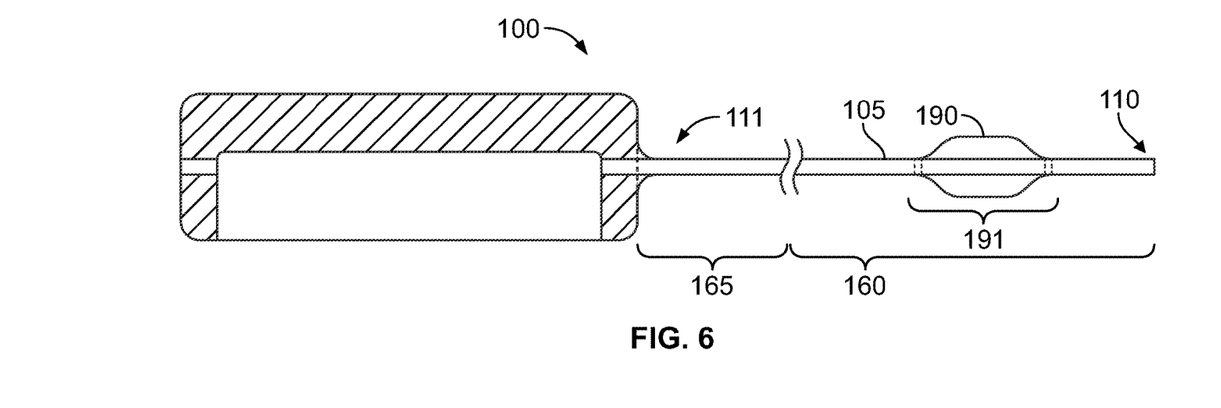
FIG. 6 is a side view of the deployment device having an inflation balloon arranged at the first end of the first catheter.

The catheter system 100 may also include a balloon 190 coupled to the first end 110 of the first catheter 105, as shown in FIG. 6. In operation, inflation of the balloon 190 may result in reversal of blood flow and more effective aspiration of the emboli. In such an example, the catheter system 100 may include a balloon inflation port and a balloon inflation lumen coupled to both the balloon 190 and the balloon inflation port. In one embodiment, the wall thickness of the first catheter 105 along the balloon inflation lumen area 191 is at least 0.3 mm and at least 0.127 mm in the other areas of the first catheter 105.

The catheter system 100 may further include a third catheter (not shown) that has a first end and a second end. The third catheter has a third diameter that is less than the second diameter and the third catheter is moveable relative to the second catheter. The third catheter may have a length ranging from about 140 cm to about 170 cm, for example. The third diameter ranges from about 0.025 mm to about 1 mm, for example, and the third diameter corresponds to an outer diameter. The third catheter may be used to cross a lesion and to introduce a stent retriever across the lesion.

The catheter system 100 may further include a plurality of flush lines (not shown) having outlets arranged at the second end 121 of the first catheter 105. The plurality of flush lines may be used to maintain constant flow of physiologically compatible solution (e.g., heparinized saline) in order to prevent formation of thrombi inside the catheters. In addition, the flush lines also beneficially provide lubrication and keep the system air-free.

In operation, an example method may include (a) introducing a guidewire into an arterial configuration 181 via arterial access, (b) loading the catheter system 100 according to any of the embodiments described above onto the guidewire, (c) moving the catheter system 100 along the guidewire and introducing the first catheter 105 into a first arterial configuration, and (d) advancing, using the wire 130 of the catheter system 100, the second catheter 115 with respect to the first catheter 105 to move the second catheter 115 into a second arterial configuration. The second arterial configuration may be a distal segment of the first arterial configuration or a branched vessel.

In one embodiment, the method may further include (e) inflating a balloon 190 coupled to the first end 110 of the first catheter 105. In another embodiment, the method may further include (f) advancing a treatment solution out of the second catheter 115 and into the second arterial configuration. In yet another embodiment, the method may further include (g) advancing a stent retriever though a third catheter and into the second or third arterial configuration. It will be appreciated that other arrangements are possible as well, including some arrangements that involve more or fewer steps than those described above, or steps in a different order than those described above.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

The invention claimed is:

1. A catheter system comprising:
   a first catheter having a first end and a second end, wherein the first catheter has a first diameter;
   a second catheter having a first end and a second end, wherein the second catheter has a second diameter that is less than the first diameter of the first catheter, and wherein the second catheter is positioned at least partially within a lumen of the first catheter and is moveable relative to the first catheter such that the first end of the second catheter can be advanced out of or retracted into the lumen of the first catheter;
   a wire having a first end and a second end, wherein the first end of the wire is directly coupled to the second end of the second catheter, wherein the second end of the second catheter is a proximal end of the second catheter; and
   a rotatable component in mechanical communication with the second end of the wire, wherein a rotation of the rotatable component in a first direction causes a first movement of the first end of the wire, wherein the first movement of the first end of the wire causes the second catheter to be advanced out of the lumen of the first catheter, wherein a rotation of the rotatable component in a second direction opposite the first direction causes a second movement of the first end of the wire, and wherein the second movement of the first end of the wire causes the second catheter to be retracted into the lumen of the first catheter.

2. The catheter system of claim 1, wherein a wall thickness of a portion of the first end of the second catheter is less than a wall thickness of a portion of the first end of the first catheter.

3. The catheter system of claim 1, wherein the first catheter comprises a first material, and wherein the second catheter comprises a second material that is different than the first material.

4. The catheter system of claim 3, wherein the first material comprises an elastomer, a metal, a hydrophilic polymer, or a combination thereof.

5. The catheter system of claim 3, wherein the second material comprises an elastomer, a metal, a hydrophilic polymer, or a combination thereof.

6. The catheter system of claim 1, wherein a stiffness of a portion of the first end of the first catheter is greater than a stiffness of a portion of the first end of the second catheter.

7. The catheter system of claim 1, wherein the first catheter comprises a plurality of braided metal strands arranged longitudinally or helically along at least a portion of a length of the first catheter.

8. The catheter system of claim 1, wherein at least one of the first catheter and the second catheter comprises a hydrophilic coating.

9. The catheter system of claim 1, wherein the first catheter includes a conduit arranged therein in which the wire at least partially resides.

10. The catheter system of claim 1, further comprising a locking system configured to lock the second catheter in place.

11. The catheter system of claim 1, wherein the first catheter is in mechanical communication with the second catheter via a rack and pinion system.

12. The catheter system of claim 1, wherein the first catheter has a length ranging from about 20 cm to about 110 cm.

13. The catheter system of claim 1, wherein the first diameter ranges from about 1.33 mm to about 9 mm.

14. The catheter system of claim 1, wherein the second catheter has a length ranging from about 10 cm to about 100 cm.

15. The catheter system of claim 1, wherein the second diameter ranges from about 1 mm to about 8.7 mm.

16. The catheter system of claim 1, wherein an overall length of the catheter system has a range of about 20 cm to about 160 cm when the second catheter is fully extended.

17. The catheter system of claim 1, wherein the wire comprises at least one braided wire.

18. The catheter system of claim 1, wherein the first end of the first catheter has a radius of curvature ranging from about 0 mm to about 170 mm.

19. The catheter system of claim 1, wherein the first end of the second catheter has a radius of curvature ranging from about 0 mm to about 170 mm.

20. The catheter system of claim 1, further comprising:
    a balloon coupled to the first end of the first catheter.

21. The catheter system of claim 1, further comprising:
    a third catheter having a first end and a second end, wherein the third catheter has a third diameter that is less than the second diameter, and wherein the third catheter is moveable relative to the second catheter.

22. The catheter system of claim 21, wherein the third catheter has a length ranging from about 140 cm to about 170 cm.

23. The catheter system of claim 21, wherein the third diameter has a range from about 0.025 mm to about 1 mm.

24. The catheter system of claim 1, further comprising a plurality of flush lines positioned on the second end of the first catheter.

25. The catheter system of claim 1, further comprising a dilator coupled to the first end of the second catheter.

26. The catheter system of claim 25, wherein the dilator has a length at least about 5 cm longer than an overall length of the catheter system when the second catheter is fully extended.

27. The catheter system of claim 1, wherein the second catheter has a first portion arranged at the first end, a second portion arranged at the second end and a third portion arranged therebetween, wherein the first portion of the second catheter has a wall thickness less than a wall thickness of the third portion of the second catheter, and wherein the wall thickness of the third portion of the second catheter is less than a wall thickness of the second portion of the second catheter.

28. The catheter system of claim 1, wherein the second catheter has a first portion arranged at the first end a second portion arranged at the second end and a third portion arranged therebetween, wherein the first portion of the second catheter has a durometer less than a durometer of the third portion of the second catheter, and wherein the durometer of the third portion of the second catheter is less than the durometer of the second portion of the second catheter.

29. The catheter system of claim 28, wherein an outer diameter of the first portion of the second catheter is equal to an outer diameter of the third portion of the second catheter.

30. The catheter system of claim 28, wherein an outer diameter of the second portion of the second catheter is greater than the outer diameter of the first portion and the outer diameter of the third portion of the second catheter.

31. The catheter system of claim 1, wherein the first catheter has a distal first section at the first end and a proximal second section at the second end, wherein the first catheter comprises an elastomer outer layer with a durometer in the distal first section that is lower than a durometer of the proximal second section.

32. A method comprising:
introducing a guidewire into an arterial configuration via arterial access;
loading the catheter system according to claim 1 onto the guidewire;
moving the catheter system along the guidewire and introducing the first catheter into a first arterial configuration; and
advancing, via the wire of the catheter system, the second catheter with respect to the first catheter to move the second catheter into a second arterial configuration.

33. The method of claim 32, further comprising:
inflating a balloon coupled to the first end of the first catheter.

34. The method of claim 32, further comprising:
advancing a treatment solution out of the second catheter and into the second arterial configuration.

35. The method of claim 32, further comprising:
advancing a stent retriever through a third catheter and into the second arterial configuration or a third arterial configuration.

36. The method of claim 32, further comprising:
advancing a coronary stent through the second catheter and into the second arterial configuration.

37. The method of claim 32, further comprising:
advancing a clot retrieval device through the second catheter for pulmonary and venous thrombectomy.

\* \* \* \* \*